(12) United States Patent
Francois et al.

(10) Patent No.: US 10,076,397 B2
(45) Date of Patent: Sep. 18, 2018

(54) GUIDE FOR SELECTING AND POSITIONING A PROSTHESIS

(71) Applicant: Sofradim Production, Trévoux (FR)

(72) Inventors: Sebastien Francois, Jassans-Riottier (FR); Sebastien Ladet, Caluire & Cuire (FR)

(73) Assignee: Sofradim Production, Trevoux (FR)

( * ) Notice: Subject to any disclaimer, the term of this patent is extended or adjusted under 35 U.S.C. 154(b) by 952 days.

(21) Appl. No.: 14/377,883

(22) PCT Filed: Mar. 22, 2013

(86) PCT No.: PCT/IB2013/000960
§ 371 (c)(1),
(2) Date: Aug. 11, 2014

(87) PCT Pub. No.: WO2013/140259
PCT Pub. Date: Sep. 26, 2013

(65) Prior Publication Data
US 2015/0018851 A1    Jan. 15, 2015

(30) Foreign Application Priority Data
Mar. 22, 2012 (FR) .................................. 12 52568

(51) Int. Cl.
*A61F 2/00* (2006.01)
*G01B 5/00* (2006.01)

(52) U.S. Cl.
CPC .............. *A61F 2/0063* (2013.01); *G01B 5/00* (2013.01); *A61F 2002/0072* (2013.01);
(Continued)

(58) Field of Classification Search
CPC ............ A61F 2/0063; A61F 2250/0097; A61F 2250/0091; A61F 2240/005;
(Continued)

(56) References Cited

U.S. PATENT DOCUMENTS 5,662,704 A * 9/1997 Gross .................... A61F 2/2412
623/2.1
2005/0100708 A1* 5/2005 McKinney ............ B28B 11/001
428/131
(Continued)

FOREIGN PATENT DOCUMENTS

FR         2864443 A1    7/2005
WO    WO2007/050382 A1    5/2007

OTHER PUBLICATIONS

International Search Report for PCT/IB13/000960 dated Aug. 5, 2013 (3 pages).

*Primary Examiner* — Katherine M Shi
*Assistant Examiner* — Michael Mendoza

(57) ABSTRACT

The invention relates to a device (1) and method for selecting the size and shape of a prosthesis and/or for determining the location of marks to be made on the external face of the skin of a patient intended to receive such a prosthesis, for example for repairing a hernia, comprising a sheet (2) of transparent material, the said sheet comprising: —a plurality of graphical representations (3*a*, 3*b*, 4*a*, 4*b*, 5*a*, 5*b*, 5*c*, 5*d*) concentrically embodying the respective outlines of various shapes and sizes of prosthesis, —a plurality of first holes (6*a*, 6*b*, 6*c*, 6*d*, 6*e*, 7*a*, 7*b*, 7*c*, 7*d*, 7*e*) arranged along the transverse line passing through the center of the said sheet, and—a plurality of second holes (8*a*, 8*b*, 8*c*, 8*d*, 8*e*, 8*f*, 8*g*, 9*a*, 9*b*, 9*c*, 9*d*, 9*e*, 9*f*, 9*g*) arranged along the longitudinal line passing through the center (C) of the said sheet.

8 Claims, 3 Drawing Sheets

Figure 1:
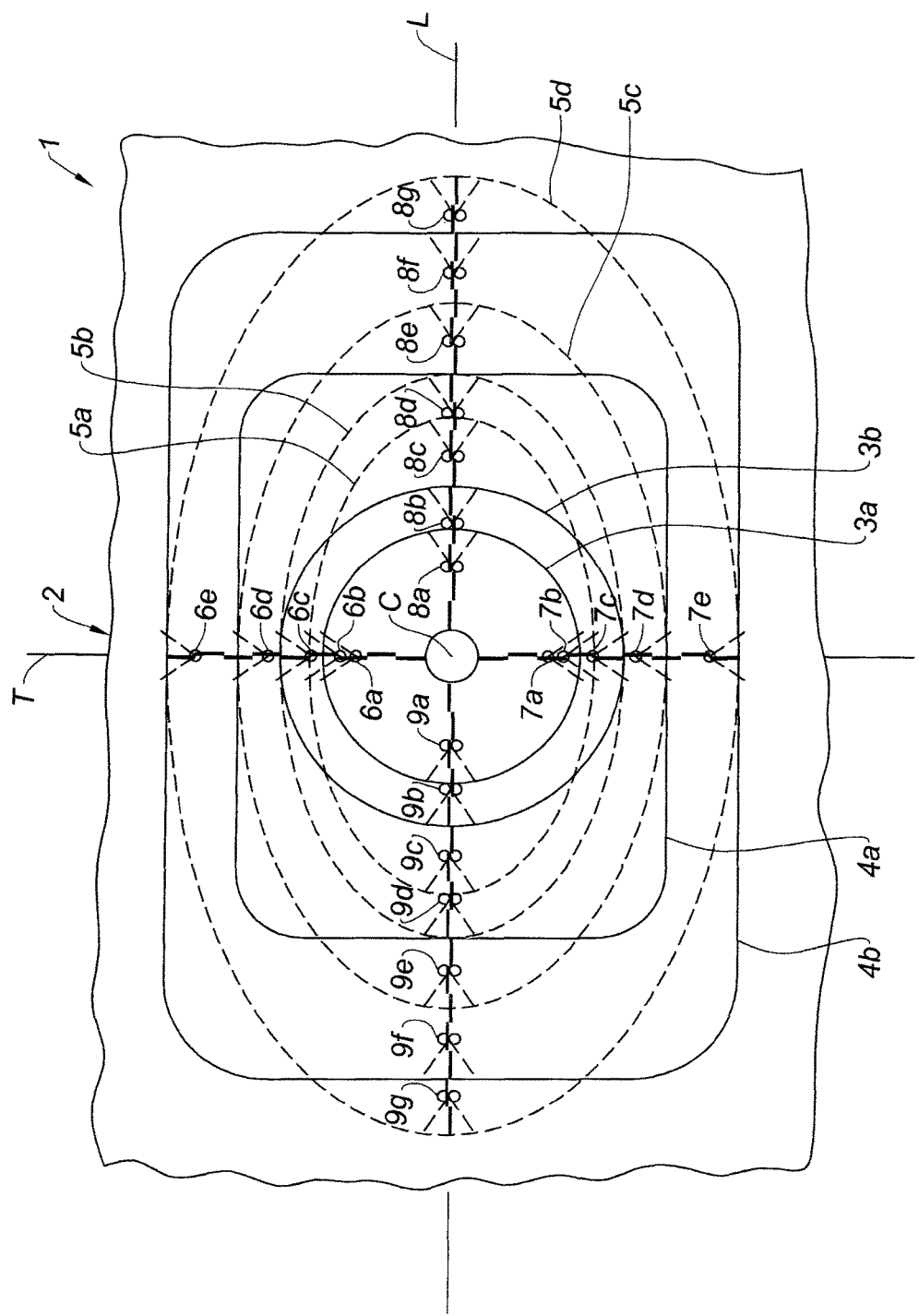

(52) U.S. Cl.
 CPC . *A61F 2240/005* (2013.01); *A61F 2250/0087* (2013.01); *A61F 2250/0091* (2013.01); *A61F 2250/0097* (2013.01)

(58) Field of Classification Search
 CPC ...... A61F 2002/0072; A61F 2250/0087; A61F 2002/4658; G01B 5/00; A61B 5/1072; A61B 5/1075; A61B 5/1076
 See application file for complete search history.

(56) References Cited

U.S. PATENT DOCUMENTS

2005/0288691 A1* 12/2005 Leiboff ................. A61F 2/0063
 606/151
2008/0167729 A1 7/2008 Nelson et al.

\* cited by examiner

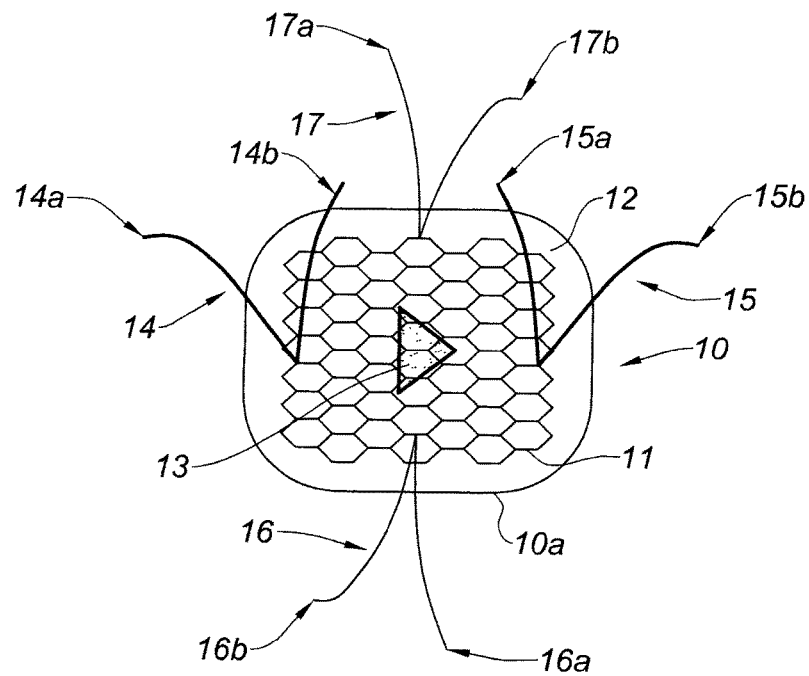
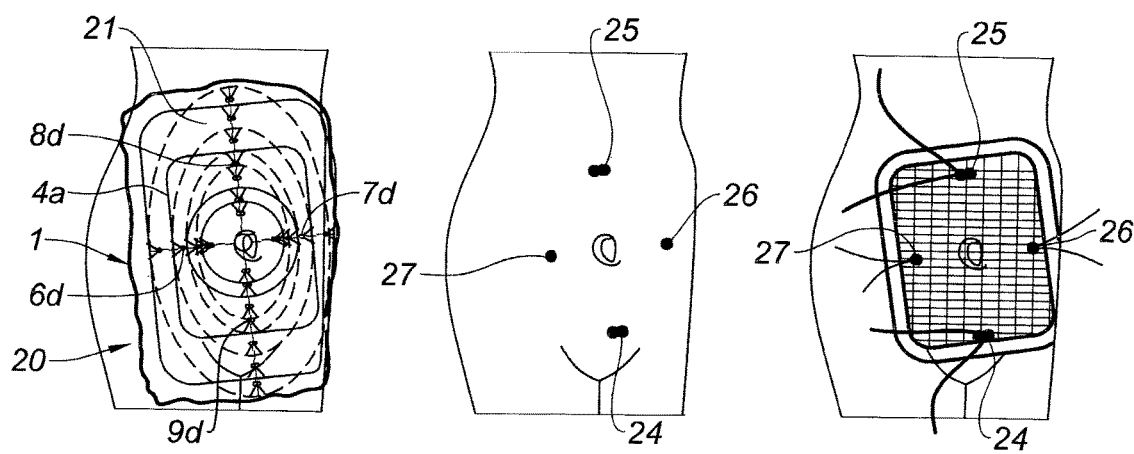
Fig. 2
Fig. 3A    Fig. 3B    Fig. 3C

GUIDE FOR SELECTING AND POSITIONING A PROSTHESIS

CROSS-REFERENCE TO RELATED APPLICATIONS

This application is a National Stage Application of PCT/1613/000960 under 35USC § 371 (a), which claims priority of French Patent Application Serial No. 12/52568 filed Mar. 22, 2012, the disclosures of each of the above-identified applications are hereby incorporated by reference in their entirety.

The present invention relates to a device for selecting the size and shape of a prosthesis and/or for determining the location of marks to be made on the external face of the skin of a patient intended to receive such a prosthesis, for example a prosthesis for repairing a hernia.

A hernia is a phenomenon which leads to a tissue defect within a wall of the human body, for example within the abdominal wall. To treat hernias, prostheses have been developed which act as wall reinforcements and are intended, temporarily or permanently, to plug the tissue defect. These prostheses generally take the form of a piece of planar overall geometric shape defining two opposite faces. In the case of a hernia in the abdominal wall for example, one face of the prosthesis is intended to be positioned facing the abdominal wall, to plug the tissue defect, the other face being intended to face the abdominal cavity.

Hernia prostheses may adopt several shapes, such as rectangular, round, oval, elliptical, depending on the anatomical structure to which these prostheses have to be adapted. In the case of hernias in the abdominal wall, because of the tissue defect that has to be treated, the prostheses more generally adopt a shape that has a longitudinal dimension, such as a rectangle or an oval. By contrast, in the case of an umbilical hernia, the prosthesis will rather be of round shape. Moreover, the dimensions of these prostheses may vary according to the size and build of the patient, according to the severity of the hernia and according to the type of hernia: thus, the dimensions of these prostheses may for example vary from 4 cm×4 cm in the case of small hernias, for example umbilical hernias, to 40 cm×30 cm in the case of larger hernias such as inguinal hernias for example.

Moreover, hernia prostheses are increasingly often being fitted using laparoscopy which involves less trauma for the patient than an open-surgery operation. In laparoscopy, the prosthesis is introduced into the body of the patient using a trocar that requires only a small incision. The prosthesis is generally folded and/or rolled up inside the trocar and then opened out at the implantation site. The implantation site is illuminated using another trocar provided for that purpose and the surgeon views the site using a camera or laparoscope which relays images of the abdominal cavity back to him. The lack of stereoscopic vision, the tight confines of the operating area available for the surgical procedure and the continuous movements of nearby internal organs make the steps of orientating the prosthesis and attaching it to the abdominal wall particularly difficult for the surgeon.

However, for reasons of effectiveness, the prostheses have to be arranged in a specific and very precise manner, in relation both to the defect being treated and to the surrounding organs at the time of implantation. For example, prostheses that have anisotropic mechanical properties have to be orientated correctly in order to comply with the natural biomechanical behaviour of the abdominal wall. Finally, the prostheses have to be attached firmly and securely to the abdominal wall in order to avoid phenomena of migration following implantation. To this end, use is advantageously made of transparietal sutures, which means sutures obtained using threads one end of which is fixed to the prosthesis, the other end passing right through the abdominal wall and the skin to be knotted to the end of another similar suture thread outside the patient's body. Once the knot has been tied, it returns under the skin on top of the muscles of the abdominal wall, leaving on the external surface of the skin only a minimum puncture mark identical to a needle prick.

Such transparietal sutures are particularly effective. However, in some instances, the surgeon may decide to supplement the attachment of the prosthesis with the use of additional clips which he attaches using laparoscopy.

Thus, it would be desirable to have available a device that allowed the surgeon to make sure that the prosthesis is correctly positioned while it is being implanted and attached and that also allowed him to determine more easily what size and shape of prosthesis to use.

The present invention seeks to address this problem by providing a device that allows selecting the size and shape of a prosthesis and that allows marks corresponding, amongst other things, to the points at which the transparietal sutures for such a prosthesis need to be made, for example for a prosthesis for repairing a hernia in the abdominal wall situated directly under a region of the skin of a patient to be marked on the external face of the said region of the skin of the patient, for example using a marker such as a felt-tip pen.

A first aspect of the present invention is a device for selecting the size and shape of a prosthesis and/or for determining the location of marks to be made on the external face of the skin of a patient intended to receive such a prosthesis, for example for repairing a hernia, comprising at least one sheet of transparent material, the said sheet being of elongate overall shape defining a longitudinal direction, a transverse direction, and a centre of the said sheet, the said sheet comprising:
  at least one plurality of graphical representations concentrically embodying the respective outlines of various shapes and sizes of prostheses, for example for repairing hernias,
  at least one plurality of first holes arranged along the transverse line passing through the centre of the said sheet, and
  at least one plurality of second holes arranged along the longitudinal line passing through the centre of the said sheet.

The device of the invention allows a surgeon to select the best size and shape of a prosthesis for a determined treatment. For example, the device of the invention allows a surgeon to select the right size and the right shape for a prosthesis intended to repair a hernia defect. The device according to the invention allows the surgeon who is to implant a prosthesis, particularly for a hernia, and who is to attach this prosthesis using transparietal sutures, to ensure that the prosthesis is correctly positioned: specifically, the device according to the invention provides the surgeon with information regarding the locations at which to make the transparietal sutures. In particular, thanks to the device according to the invention, the surgeon may, using a marker such as a felt-tip pen, mark the external surface of a region of the skin of the patient with marks that correspond directly to preferred locations for suturing a prosthesis, for example a prosthesis intended to repair a hernia in the abdominal wall facing the said region. Although the present application more particularly describes the example of prostheses used for repairing hernias, the device according to the invention can be applied to determining the location of marks to be made on the external face of the skin of a patient intended to receive any prosthesis, whether this prosthesis is for repairing a hernia or for some other complaint.

Another aspect of the present invention is a method for selecting the size and shape of a prosthesis, for example for treating a hernia defect, comprising the following steps:
  i) a device as described herein is provided,
  ii) the device is applied to the external face of the region of the skin of the patient, for example under which the hernia defect is located, and the centre of the sheet of material of the device is substantially aligned on the site of the hernia defect,
  iii) the sheet of material is pivoted so as to select the graphical representation corresponding to a size and shape of a prosthesis constituting the best coverage of the hernia defect.

Another aspect of the invention is a method for determining the location of marks to be made on the external face of the skin of a patient intended to receive a prosthesis, for example for treating a hernia defect, comprising the following steps:
  i) a device as described herein is provided,
  ii) the device is applied to the external face of the region of the skin of the patient, for example under which the hernia defect is located, and the centre of the sheet of material of the device is substantially aligned on the site of the hernia defect,
  iii) the sheet of material is pivoted so as to select the graphical representation corresponding to a size and shape of a prosthesis constituting the best coverage of the hernia defect,
  iv) using the first and second holes of the device, the said skin is marked in the transverse direction of the sheet and in the longitudinal direction of the sheet.

Another aspect of the present invention is a method for treating a hernia defect comprising the following steps:
  a) marks are applied on the external face of the skin of a patient according to the method described above,
  b) a prosthesis having the size and shape corresponding to the selected graphical representation above is provided,
  c) the prosthesis of step b) is conveyed to the implantation site and positioned to cover the hernia defect,
  d) suturing instrument(s) are introduced into the skin of the patient from the outside at the mark(s) applied in step a) in order to complete transparietal suture(s) for attaching the prosthesis to the abdominal wall.

In embodiments, prior to step c), the prosthesis is provided with suture threads which are pre-stitched at the preferred points on the prosthesis at which to make the future transparietal sutures.

In embodiments, in step d), a transparietal suture is performed by catching two free ends of one pre-stitched suture thread, pulling these two ends outside the patient, tying a knot with said two ends and releasing the knot formed into the abdominal wall.

When a surgeon needs to repair a hernia in the abdominal wall for example, he applies the device according to the invention to the external face of the region of the skin of the patient under which the hernia is located. By touch or palpation, and/or alternatively thanks to the light of a laparoscope, the surgeon determines substantially where the hernia defect is situated on the abdominal wall beneath the skin of the patient. Because of the transparency of the material of which the said sheet is made, the surgeon can easily position the centre of the sheet more or less aligned on the site of the hernia defect. The surgeon can then pivot the sheet of material, assisted by the graphical representations of the said sheet which embody the outlines of various shapes and sizes of prosthesis until he obtains what, in his opinion, constitutes the best coverage of the hernia defect: he thus selects a preferred size and preferred shape of prosthesis from the prosthesis sizes and shapes that correspond to the graphical representations, for covering and thus treating the hernia defect. Using the first and second holes he can mark the skin of the patient with a marker, for example with a felt-tip pen, so that the said skin is marked both in the transverse direction of the sheet, which corresponds to a transverse plane in the human body, and in the longitudinal direction of the sheet, which corresponds to a sagittal plane of the human body. These marks will allow him, when the time comes to attach the prosthesis to the abdominal wall, to ensure that the transparietal sutures, both transverse and sagittal, are made at the optimum points.

Thus, having marked the skin of the patient as indicated hereinabove, the surgeon prepares a prosthesis of the size and shape determined using the device according to the invention as explained above. For example, if appropriate, the surgeon pre-stitches the prosthesis with suture threads at the preferred points on the prosthesis at which to make the future transparietal sutures. The prosthesis with its pre-stitched suture threads is introduced onto the implantation site laparoscopically using a trocar as described above. The prosthesis is opened out to cover the hernia defect that is to be treated. Using one or more suturing instruments such as needles with eye or hook, that are introduced into the skin of the patient from the outside at the mark applied by the surgeon, and which then pass through the abdominal wall, the surgeon catches hold of two free ends of pre-stitched suture threads, pulls these two ends outside the patient, ties a knot and releases the knot formed into the abdominal wall. The transparietal suture thus made is firm and effective and is optimally located thanks to the use of the device according to the invention. The surgeon repeats this procedure for all of the marks he has made on the skin of the patient and can thus be assured that the prosthesis is correctly positioned on and firmly attached to the abdominal wall.

In one embodiment of the invention, the said first holes all have the same first shape, the said second holes all have the same second shape, the said first shape being different from the said second shape. Thus, when the surgeon is making his marks on the skin, he can immediately identify whether the mark in question is transverse or rather sagittal in relation to the body of the patient. Moreover, if the prosthesis being used to repair the hernia has pre-stitched suture threads in different colours according to whether the suture is supposed to be a transverse suture or a sagittal suture, the surgeon can immediately identify whether or not the threads and the marks match.

For example, with the said first holes having the shape of a disc, the said second holes have the shape of a double disc. Alternatively or in combination, the said first holes have an edging of a first colour, the said second holes have an edging of a second colour, the said first colour being different from the said second colour. Thus, it is an immediate and simple matter to distinguish between the holes of the transverse line and the holes of the longitudinal line.

For example, the said first and second holes correspond to preferred locations for stitches of suture for the prostheses, for example for repairing hernias, having outlines corresponding to those embodied by the said graphical representations. For example, one pair of first holes and one pair of second holes correspond to each outline embodied, each hole of one pair being symmetric with the other hole of the said pair about the centre of the said sheet. Thus, four holes situated at four cardinal points of the said sheet may correspond to each outline.

In one embodiment of the invention, the said graphical representations are produced in a colour that is different from the said first and second colours. Such an embodiment allows an immediate and easy distinction to be made between the graphical representations of the transverse and longitudinal lines on which the first and second holes lie.

Another aspect of the invention relates to a kit comprising at least one device described hereinabove and at least one prosthesis, for example for repairing a hernia, the said prosthesis having an outline corresponding to one of those embodied by the said graphical representations.

In one embodiment, the said prosthesis comprises pre-stitched suture threads, the said pre-stitched suture threads being located at the points on the prosthesis that lie facing the said corresponding first and second holes when the said prosthesis is applied to the said sheet of material with its outline aligned with that of the corresponding graphical representation.

Thus, when applying and securing the prosthesis, the pre-stitched suture threads are situated in line with the marks made by the surgeon on the skin of the patient. The surgeon therefore knows exactly where he has to insert the suturing instruments in order to catch hold of the free ends of the suture threads in order to tie the knot in the transparietal suture.

In one embodiment, the said prosthesis comprises a central marking indicating the longitudinal direction of the prosthesis: this marking may serve to indicate to the surgeon how to position the prosthesis with respect to the caudal direction and with respect to the cranial direction of the human body in which the prosthesis is implanted.

Specifically, it may be beneficial for these prostheses to be provided with marking means, aimed at providing the surgeon with information regarding the special properties of one face of the prosthesis or alternatively regarding the dimensions or the location of a specific point of the prosthesis.

Thus, depending on the environment of the implantation site, for example where the viscera, soft tissues, etc., are present, it may be important for the surgeon to be given information at a given point on the prosthesis so that the surgeon can plan to arrange the prosthesis in a particular orientation or alternatively to arrange a certain region of the prosthesis facing such an organ or, on the other hand, as far away as possible from such an organ, etc.

In one embodiment, the suture threads situated facing the said first holes are in a different colour from the suture threads situated facing the said second holes. Thus, the surgeon can immediately see that the threads he has retrieved using the suture instruments are indeed the threads he is seeking to retrieve.

Figure 4:
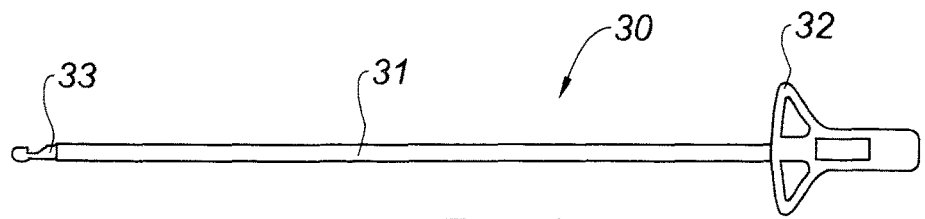
Figure 5A:
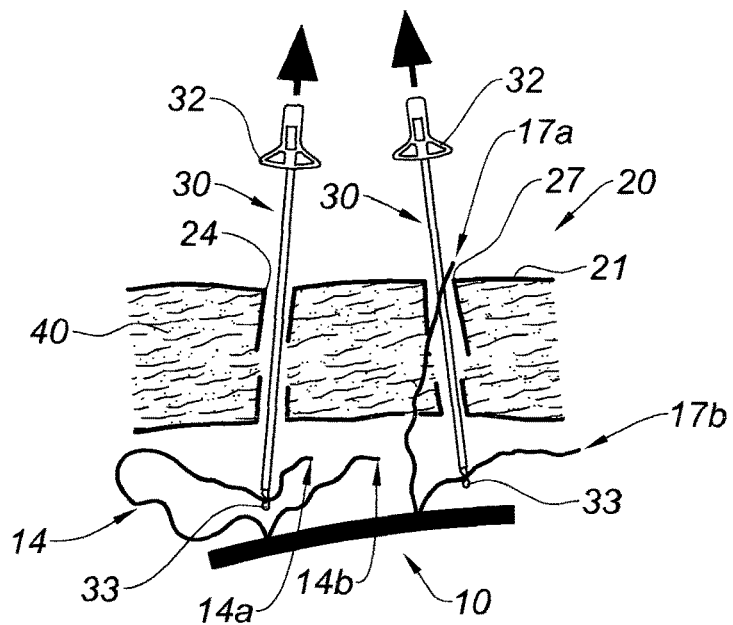
Figure 5B:
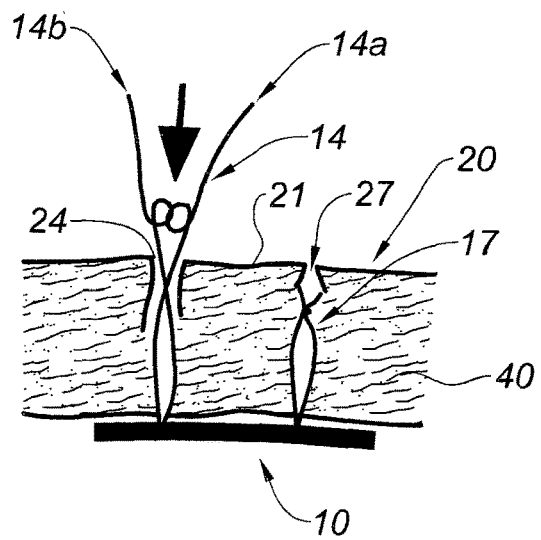

The advantages of the present invention will become more clearly apparent in the light of the following description and of the attached drawings in which:

FIG. 1 is a view from above of a device according to the invention,

FIG. 2 is a view from above of a prosthesis that can be used with the device according to the invention, FIGS. 3A-3C are diagrams showing three steps in the procedure for using the device according to the invention in a method for treating a hernia in the abdominal wall, FIG. 4 is a side view of a suturing instrument that can be used in the method of treating a hernia using the device according to the invention, FIGS. 5A and 5B are two diagrams illustrating the step of attaching a prosthesis in the method of treating a hernia using the device according to the invention.

Reference is made to FIG. 1 which depicts a device 1 according to the invention comprising a sheet 2 of transparent material. As will become apparent from the description which follows, the device 1 makes it possible to determine the location of marks to be made on the external face of the skin of a patient intended to receive a prosthesis for repairing a hernia. In other embodiments which have not been depicted, the prosthesis could bear information other than that for repairing a hernia.

The transparent material constituting the sheet 2 may be chosen from polyethylene (PE), polyurethane (PU), polyvinyl chloride (PVC), polymethacrylate (PMA) and derivatives and mixtures thereof. The sheet 2 is flexible and easy to handle. In particular, the sheet 2 is compliant which allows it to conform to the external anatomical shape of a human body, particularly in the abdominal region.

With reference to FIG. 1, the sheet 2 has an elongate overall shape defining a longitudinal direction, a transverse direction and a centre C. In FIG. 1, the sheet 2 is in the shape of a rectangle. As an alternative, the sheet could be of oval shape.

The sheet 2 is provided with a plurality of graphical representations concentrically embodying the respective outlines of various shapes and sizes of prosthesis for use in hernia repair. In the example depicted in FIG. 1, the sheet 2 thus comprises:

two concentric circles (3a, 3b) of centre C, representing the respective outlines of two round prostheses of different sizes, two rectangles (4a, 4b) with the same centre C, representing the respective outlines of two rectangular prostheses of different sizes, four concentric ellipses (5a, 5b, 5c, 5d) of centre C, representing the respective outlines of four elliptical prostheses of different sizes.

The sheet 2 is additionally provided with a plurality of first holes (6a, 6b, 6c, 6d, 6e, 7a, 7b, 7c, 7d, 7e) arranged along the transverse line T passing through the centre C of the sheet 2: in the example depicted, the plurality of first holes comprises a first series of five first holes (6a, 6b, 6c, 6d, 6e) arranged symmetrically about the centre C with respect to a second series of five first holes (7a, 7b, 7c, 7d, 7e). The first holes (6a, 6b, 6c, 6d, 6e, 7a, 7b, 7c, 7d, 7e) all have the same shape, namely the shape of a disc. Alternatively, these first holes could have the shape of a square, of a rectangle, of a star, etc., provided that their shape allows a marker to pass through the sheet of material and leave a mark on a support to which the sheet 2 is applied, as will be seen later on in this description.

Likewise, the first holes could be other than ten in number: as will become apparent later on, the first holes serve to indicate a mark where a suture is to be made for a given prosthesis: thus, the number of first holes made in the sheet 2 is connected with the number of outlines (3a, 3b, 4a, 4b, 5a, 5b, 5c, 5d) represented on the sheet 2 and corresponding to prostheses of different shapes and sizes.

The sheet 2 is additionally provided with a plurality of second holes (8a, 8b, 8c, 8d, 8e, 8f, 8g, 9a, 9b, 9c, 9d, 9e, 9f, 9g) arranged along the longitudinal line L passing through the centre C of the sheet 2: in the example depicted, the plurality of second holes comprises a first series of seven second holes (8a, 8b, 8c, 8d, 8e, 8f, 8g) arranged symmetrically about the centre C with respect to a second series of seven second holes (9a, 9b, 9c, 9d, 9e, 9f, 9g). The second holes (8a, 8b, 8c, 8d, 8e, 8f, 8g, 9a, 9b, 9c, 9d, 9e, 9f, 9g) all have the same shape, namely the shape of a double disc. Alternatively, these second holes could have the shape of a square, of a rectangle, of a star, etc., provided that their shape allows a marker to pass through the sheet of material to leave a mark on a support to which the sheet 2 is applied, as will be seen later on in this description.

Likewise, the second holes could be other than fourteen in number: as will become apparent later on, the second holes serve to indicate a mark where a suture is to be made for a given prosthesis: thus, the number of second holes made in the sheet 2 is connected with the number of outlines (3a, 3b, 4a, 4b, 5a, 5b, 5c, 5d) represented on the sheet 2 and corresponding to prostheses of different shapes and sizes.

In the example depicted, and for preference, the second holes have a different shape from the first holes so that they can be quickly and easily distinguished from the said first holes.

For example, the first holes (6a, 6b, 6c, 6d, 6e, 7a, 7b, 7c, 7d, 7e) may have an edging in a first colour, for example red, and the second holes (8a, 8b, 8c, 8d, 8e, 8f, 8g, 9a, 9b, 9c, 9d, 9e, 9f, 9g) have an edging in a second, different, colour, for example green. Thus, the first holes are readily distinguishable and discernible from the second holes.

As will become apparent from the remainder of the description, the first and second holes correspond to preferred locations for stitches of suturing for prostheses for the repair of hernias having outlines (3a, 3b, 4a, 4b, 5a, 5b, 5c, 5d) corresponding to those embodied by the said graphical representations on the sheet 2. In one embodiment, the graphical representations, and therefore the outlines (3a, 3b, 4a, 4b, 5a, 5b, 5c, 5d) are made in a different colour from the said first and second colours, for example in blue. Thus, the surgeon can quickly differentiate with the naked eye between i) the outlines corresponding to the prostheses that can be used, ii) the first holes that indicate the marks to be made for a first set of transparietal sutures, for example the future transverse transparietal sutures, and iii) the second holes that indicate the marks to be made for a second set of transparietal sutures, for example the future sagittal transparietal sutures. Alternatively, depending on the final orientation chosen by the surgeon for the prosthesis to be implanted, the first holes may indicate the marks to be made for the future sagittal transparietal sutures and the second holes may indicate the marks to be made for the future transverse transparietal sutures.

The transverse line T and longitudinal line L of the sheet 2 may also be provided with measurement strokes so that they can be used as rules to determine the preferred dimensions of the prosthesis to be used.

One example of a prosthesis 10 that can be used with the device 1 according to the invention of FIG. 1 is depicted with reference to FIG. 2. The prosthesis 10 has an outline 10a corresponding for example to the outline 4a drawn on the sheet 2 of the device 1 of FIG. 1. Thus, the prosthesis 10 is a rectangular prosthesis. In the example depicted, the prosthesis 10 is formed of a mesh 11 covering one side of a non-stick film 12. The prosthesis 10 is provided at its centre with a triangular mark 13, one corner of the triangle pointing in the longitudinal direction of the prosthesis 10: as will become apparent from the description which follows, such a mark 13 is useful for the surgeon as he positions the prosthesis at the time of implantation.

The prosthesis 10 of FIG. 2 is additionally provided with suture threads (14, 15, 16, 17) which are pre-stitched for example on the mesh 11. The threads 14 and 15 are stitched at points which are symmetric about the centre of the prosthesis 10 and arranged on a longitudinal line passing through the centre of the prosthesis 10, near to the edge of the prosthesis 10. Each thread is stitched to the mesh 11 via its central region, and thus has two free ends (14a, 14b; 15a, 15b). In the example shown, for a implanted orientation of the prosthesis 10 corresponding to that shown on FIG. 3C, the pre-stitched threads (14, 15) located along the longitudinal line of the prosthesis 10 are intended to form the future sagittal transparietal sutures when the prosthesis is being attached to the abdominal wall. The threads 16 and 17 are stitched at points which are symmetric about the centre of the prosthesis 10 and arranged on a transverse line passing through the centre of the prosthesis 10 near to the edge of the prosthesis 10. Each thread is stitched to the mesh 11 via its central region, and thus has two free ends (16a, 16b; 17a, 17b). The threads (14, 15) pre-stitched to the longitudinal line are of a different colour from the threads (16, 17) pre-stitched to the transverse line. In the example shown, for a implanted orientation of the prosthesis 10 corresponding to that shown on FIG. 3C, the pre-stitched threads (16, 17) positioned on the transverse line of the prosthesis 10 are intended to form the future transverse transparietal sutures when the prosthesis is being attached to the abdominal wall.

Alternatively, if the prosthesis 10 is intended to be implanted in an orientation perpendicular to that shown on FIG. 3C, then, the pre-stitched threads (14, 15) located along the longitudinal line of the prosthesis 10 are intended to form the future transverse transparietal sutures when the prosthesis is being attached to the abdominal wall, whereas the pre-stitched threads (16, 17) positioned on the transverse line of the prosthesis 10 are intended to form the future sagittal transparietal sutures.

For example, with reference to FIG. 2 and with a implantation corresponding to that of FIG. 3C, the threads (14, 15) intended for the sagittal sutures are in the same first colour, and the threads (16, 17) intended for the transverse sutures are in the same second colour, the first colour being different from the second colour.

The use of the device 1 according to the invention of FIG. 1 for selecting the size and shape of a prosthesis and for determining the location of marks to make on the external face of the skin of a patient intended to receive such a prosthesis for repairing a hernia, namely the prosthesis 10 of FIG. 2 in the case of the present example, and for making the said marks on the skin of the patient, will now be described with reference to FIGS. 3A and 3B.

With reference to FIG. 3A, a surgeon who is to repair a hernia in a patient 20 takes the device 1 and applies it to the exterior face of the region of the skin 21 of the patient 20 in the vicinity of the hernia that is to be treated. Because of the flexibility of the sheet 2, the surgeon can apply it to the skin conforming to the contours thereof. Moreover, because of the transparency of the sheet 2, the surgeon can still see the skin 21 through the device 1. Moreover, by touch or palpation, or with the help of the light of a laparoscope, he knows more or less where the hernia is situated on the abdominal wall beneath the skin 21. Thus, he can determine more or less where the defect to be treated lies and places the centre C of the sheet 2 more or less at this hernia defect, as shown in FIG. 3A. The surgeon can then pivot the device 1 as he desires in order to position it in an optimal orientation so that the graphical representations of the sheet 2 cover the hernia defect. In so doing, the surgeon chooses one of the represented outlines (3a, 3b, 4a, 4b, 5a, 5b, 5c, 5d) as being the optimal outline. The surgeon thereby selects the best size and shape for the prosthesis 10 to be implanted in view of obtaining the best coverage of the hernia defect.

In the case of the present example, the surgeon chooses the outline 4a of the device 1, corresponding to the size and shape of prosthesis 10 of FIG. 2. First and second optimal holes for determining the points at which the transparietal sutures are to be made for a prosthesis corresponding to the outline 4a correspond to the outline 4a. With reference to FIG. 1, for example, in the case of the outline 4a, the corresponding first holes, namely those situated on the transverse line T, are the first holes 6d and 7d which are symmetric with one another about the centre C and each of which lie inside the outline 4a near to this said outline 4a. Likewise, and still in the case of this outline 4a, the corresponding second holes, namely those situated on the longitudinal line L, are the second holes 8d and 9d, which are symmetric with one another about the centre C and each situated inside the outline 4a, near to this said outline 4a.

In one embodiment which has not been depicted, in which the surgeon has chosen a prosthesis of round shape the outline of which corresponds to the outline 3a represented on the sheet 2 of the device of FIG. 1, the corresponding first holes would be the first holes 6a or 6b and 7a or 7b, and the corresponding second holes would be the second holes 8a and 9a. In another example which has not been depicted, in which the surgeon has chosen a prosthesis of elliptical shape, the outline of which corresponds to the outline 5c represented on the sheet 2 of the device of FIG. 1, the corresponding first holes would be the first holes 6d and 7d and the corresponding second holes would be the second holes 8e and 9e.

Thus, certain first holes and certain second holes may correspond to several represented outlines and therefore to several possible prostheses.

With reference to FIG. 3A, once the surgeon has chosen the outline 4a, the respective positions of the corresponding first holes and second holes allow him thus to determine the location of the marks to be made on the external face of the skin of the patient, which marks will let him know where to make the transparietal sutures during the operation of attaching the prosthesis 10. The surgeon takes up a marker, such as a felt-tip pen, for example, and, through each of the first holes 6d and 7d and each of the second holes 8d and 9d, draws on the skin 21 of the patient 20 a disc, in the case of the said first holes, or a double-disc, in the case of the said second holes. Then he removes the device 1. The marks (24, 25, 26 and 27) on the patient's skin are then revealed on the skin 21 of the patient 20 as shown in FIG. 3B.

Because of the different shapes of the first holes and of the second holes, marks aligned in a sagittal plane have a different shape from marks aligned in the transverse plane. As an alternative or in combination, the surgeon could also use two felt-tip pens of different colours to draw the various marks: thus, for drawing the sagittal marks in the example shown, he can use a felt-tip pen of the same colour as the suture threads intended for the sagittal sutures, and for drawing the transverse marks he can use a felt-tip pen of the same colour as the suture threads intended for the transverse sutures: such an embodiment allows the surgeon immediately to check that the prosthesis is correctly positioned and that the sagittal and transverse transparietal sutures match, at the time of the prosthesis attachment step.

The surgeon then takes hold of the prosthesis 10 of FIG. 2. The prosthesis 10 is rolled up on itself and then slipped into a trocar to be conveyed to the implantation site. This step is a step that is conventional in laparoscopic surgery and is not described in greater detail here.

The surgeon opens out and positions the prosthesis 10 using the mark 13 of the prosthesis 10 and the difference in colour of the suture threads (14, 15, 16 and 17) that allow him to orientate the prosthesis 10 correctly in the cranial-caudal direction of the body of the patient.

FIG. 3C shows, outside the body of the patient for the sake of clarity, the prosthesis 10 once it has been correctly positioned on the implantation site, at the abdominal wall that has the hernia defect that needs to be repaired, under the skin of the patient, prior to securing.

For the step of attaching the prosthesis to the abdominal wall, the surgeon will make use of the marks (24, 25, 26 and 27) which have been made using the device 1 according to the invention as described above. To do that, the surgeon will need suturing instruments like those depicted in FIG. 4. With reference to this figure, a suturing instrument 30 comprising a needle 31 which at one of its ends has a handle 32 for holding and at its opposite end has a hook 33 is depicted. Alternatively, the hook 33 could be replaced by an eye.

Reference is made to FIG. 5A which depicts, in cross section, the prosthesis 10 at the implantation site facing the abdominal wall 40 situated under the skin 21 of the patient 20. In this figure, two pre-stitched suture threads, for example one sagittal suture thread 14 and one transverse suture thread 17 have been depicted, together with their respective free ends (14a, 14b; 17a, 17b).

In order to make a sagittal transparietal suture for the purposes of attaching the prosthesis 10 to the abdominal wall 40, the surgeon takes hold of a suturing instrument 30 by its handle 32 and punctures the skin 21 with the end of the instrument 30 that is provided with the hook 33 for example at the mark 24: the hook 33 passes through the skin 21 and then the abdominal wall to emerge at the implantation site, as shown in FIG. 5A. Using tools that have not been depicted, the surgeon then slips the free end 14a of the suture thread 14 into the hook 33 then withdraws the suturing instrument 30 in the direction of the arrow depicted in FIG. 5A to bring this free end 14a outside of the patient 20. The surgeon then repeats this operation as many times as necessary in order to bring all of the free ends of all of the suture threads (14, 15, 16, 17) to outside the patient 20, each time puncturing the skin at the marks (24, 25, 26, 27) made on the skin of the patient 20.

In FIG. 5a, the free end 14a of the suture thread 14 has been slipped into the hook 33 which has not yet been brought back outside the patient 20, and the end 14b of the suture thread 14 has not yet been slipped into the hook 33 of a suturing instrument 30. By contrast, it can be seen that the free end 17a of the suture thread 17 has already been brought back outside the patient 20, whereas the free end 17b of the suture thread 17 has been slipped into the hook 33 of a suturing instrument 30.

When both free ends of the same suturing thread have been brought back outside of the patient, the surgeon ties a knot with these two ends. Thus, with reference to FIG. 5B, the tying of the knot using the free ends (14a, 14b) of the suture thread 14 is depicted. When the knot has been tied, the surgeon cuts off the excess lengths of thread and the knot returns into the abdominal wall 40 as shown in FIG. 5B in the case of the knot already formed in the suture thread 17. The surgeon thus makes particularly effective transparietal sutures. As can be seen from FIG. 5B, thanks to such sutures, the prosthesis 10 is pressed perfectly against the abdominal wall 40 and can thus perfectly cover the hernia defect (not depicted). Moreover, such sutures leave only a minimal mark of a needle prick on the surface of the skin at the site of the mark 27 for example in the case of the suture thread 17.

Thus, the device of the invention allows a surgeon to select the size and shape of a prosthesis for a determined treatment. In particular, the device of the invention allows a surgeon to select the optimal size and shape of a prosthesis for providing the best coverage of a hernia defect in the treatment of a hernia. In addition, the device according to the invention allows the surgeon who is to fit a prosthesis, for example for a hernia, and is to attach this prosthesis using transparietal sutures, to ensure that the prosthesis is correctly positioned thanks to the creation of marks located at strategic points on the skin of the patient: specifically, thanks to the marks thus made, the surgeon knows exactly where on the skin of the patient he is to puncture with the instruments in order to create the transparietal sutures. Moreover, the marks obtained using the device according to the invention also allow the surgeon immediately to discriminate the sagittal sutures from the transverse sutures that he has to perform when attaching the prosthesis to the abdominal wall.

The invention claimed is:

1. A kit comprising
at least one prosthesis, the prosthesis having an outline and
at least one external device for determining the location of marks to be made on an external face of a skin of a patient intended to receive the at least one prosthesis, the external device comprising at least one sheet of transparent material, the sheet being of elongate overall shape defining a longitudinal direction, a transverse direction, and a center of the sheet, the sheet comprising a plurality of concentric graphical representations of various shapes and sizes, a plurality of first holes arranged along a transverse line passing through the center of the sheet, and a plurality of second holes arranged along a longitudinal line passing through the center of the sheet, wherein the at least one prosthesis comprises pre-stitched suture threads, the pre-stitched suture threads being located at points on the at least one prosthesis that lie facing the corresponding first and second holes when the at least one prosthesis is applied to the sheet of material with the outline of the at least one prosthesis aligned with at least one of the graphical representations having a corresponding shape and size.

2. The kit according to claim 1 wherein the at least one prosthesis comprises a central marking indicating the longitudinal direction of the prosthesis.

3. The kit according to claim 1 wherein the suture threads situated facing the first holes are in a different color from the suture threads situated facing the second holes.

4. The kit according to claim 1, wherein the first holes all have a first shape that is the same, the second holes all have a second shape that is the same, the first shape being different from the second shape.

5. The kit according to claim 4, wherein the first holes have a shape of a disc, the second holes have a shape of a double disc.

6. The kit according to claim 5 wherein the first holes have an edging of a first color, the second holes have an edging of a second color, the first color being different from the second color.

7. The kit according to claim 6, wherein the graphical representations are produced in a color that is different from the first and second colors.

8. The kit according to claim 1, wherein the concentric graphical representations of various shapes and sizes comprise two concentric circles, two rectangles, and four concentric ellipses.

* * * * *